United States Patent
Konishi

(10) Patent No.: US 11,160,747 B2
(45) Date of Patent: Nov. 2, 2021

(54) UNEVENNESS CORRECTION COSMETIC

(71) Applicant: SHIN-ETSU CHEMICAL CO., LTD., Tokyo (JP)

(72) Inventor: Masayuki Konishi, Tokyo (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 0 days.

(21) Appl. No.: 16/482,912

(22) PCT Filed: Jan. 26, 2018

(86) PCT No.: PCT/JP2018/002386
§ 371 (c)(1),
(2) Date: Aug. 1, 2019

(87) PCT Pub. No.: WO2018/143061
PCT Pub. Date: Aug. 9, 2018

(65) Prior Publication Data
US 2019/0350835 A1 Nov. 21, 2019

(30) Foreign Application Priority Data
Feb. 2, 2017 (JP) .............................. JP2017-017479

(51) Int. Cl.
| | |
|---|---|
| *A61K 8/891* | (2006.01) |
| *A61K 8/02* | (2006.01) |
| *A61K 8/06* | (2006.01) |
| *A61K 8/25* | (2006.01) |
| *A61K 8/895* | (2006.01) |
| *A61K 8/92* | (2006.01) |
| *A61Q 1/02* | (2006.01) |

(52) U.S. Cl.
CPC .............. *A61K 8/891* (2013.01); *A61K 8/025* (2013.01); *A61K 8/06* (2013.01); *A61K 8/25* (2013.01); *A61K 8/895* (2013.01); *A61K 8/92* (2013.01); *A61Q 1/02* (2013.01); *A61K 2800/10* (2013.01); *A61K 2800/43* (2013.01)

(58) Field of Classification Search
CPC ................................. A61K 8/891; A61K 8/894
See application file for complete search history.

(56) References Cited

U.S. PATENT DOCUMENTS

| | | | |
|---|---|---|---|
| 2002/0022037 A1 | 2/2002 | Kurosawa et al. | |
| 2006/0034875 A1* | 2/2006 | Nakanishi | A61K 8/891 |
| | | | 424/401 |
| 2011/0217250 A1 | 9/2011 | Hayakawa et al. | |
| 2011/0301247 A1 | 12/2011 | Hayakawa et al. | |
| 2013/0287824 A1 | 10/2013 | Inaba | |

FOREIGN PATENT DOCUMENTS

| | | |
|---|---|---|
| EP | 2100591 A2 | 9/2009 |
| JP | 2000-16919 A | 1/2000 |
| JP | 3652843 B2 | 5/2005 |
| JP | 2015-86196 A | 5/2015 |
| JP | 2015-193564 A | 11/2015 |
| JP | 5893896 B2 | 3/2016 |
| JP | 2016-124846 A | 7/2016 |
| JP | 2016-210712 A | 12/2016 |
| JP | 2016-222599 A | 12/2016 |
| JP | 2017-2016 A | 1/2017 |
| WO | WO 2016/030838 A1 | 3/2016 |

OTHER PUBLICATIONS

English language translation JP 2015/086196, May 2015.*
English language translation JP 2015/193564, Nov. 2015.*
"Hybrid Silicone Powders for Oil Absorption in Cosmetics", cosmeticandtoiletries.com, Feb. 2012 (Year: 2012).*
International Search Report issued in PCT/JP2018/002386 (PCT/ISA/210), dated Mar. 13, 2018.
Written Opinion of the International Searching Authority issued in PCT/JP2018/002386 (PCT/ISA/237), dated Mar. 13, 2018.
Extended European Search Report, dated Oct. 28, 2020, for European Application No. 18747926.6.

* cited by examiner

*Primary Examiner* — Margaret G Moore
(74) *Attorney, Agent, or Firm* — Birch, Stewart, Kolasch & Birch, LLP

(57) ABSTRACT

Provided is a cosmetic product that has excellent unevenness correction effect, feel on use, spread (spreadability), and adherability, and that leaves no powdery residues. This unevenness correction cosmetic comprises (a) a partially crosslinked organopolysiloxane, (b) oil-absorbing silicone composite spherical powder, and 8-85 mass % of (c) an oil solution having a viscosity of 1-100 mm$^2$/s at 25° C., wherein the total amount of component (a) and component (b) is 10-35 mass %, and the mass ratio of component (a) to component (b) as represented as (a)/(b) is 0.02-0.55.

10 Claims, No Drawings

_(10)_ US 11,160,747 B2

UNEVENNESS CORRECTION COSMETIC

TECHNICAL FIELD

This invention relates to an uneven texture-correcting cosmetic composition. It is noted that a composition for cosmetic formulation or a cosmetic composition is sometimes described as cosmetic.

BACKGROUND ART

In the past, there were developed cosmetics for flattening irregularities of varying size on the skin (resulting from various causes) to make them less conspicuous in order that the skin texture look esthetic.

For example, the technique for burying recesses and flattening protrusions on the skin by using a composition containing a powder having a low refractive index and a silicone oil having a high viscosity is known from Patent Document 1: JP 3652843. However, the high viscosity silicone oil is substantially detrimental to the oil absorption of the powder, there are found powder residues, poor retention and poor transparency.

Also the technique of achieving an uneven texture-correcting effect and improving retention by formulating a film former is known from Patent Document 2: JP-A 2000-016919 and Patent Document 3: JP 5893896. These compositions, however, are unfavorable because of perception of a feeling inherent to the film former and difficult spreading on the skin. Also, no studies have been made for improving the feel-on-use, adhesion and residual powdery feeling of these uneven texture-correcting cosmetic compositions by adjusting the ratio of crosslinked silicone to spherical powder.

PRIOR ART DOCUMENTS

Patent Documents

Patent Document 1: JP 3652843
Patent Document 2: JP-A 2000-016919
Patent Document 3: JP 5893896

SUMMARY OF INVENTION

Technical Problem

An object of the invention, which has been made under the above-mentioned circumstances, is to provide a cosmetic composition featuring an uneven texture-correcting effect, feel-on-use, spreading or extension, and adhesion, and leaving no powder residues.

Solution to Problem

Making extensive investigations to attain the above object, the inventor has found that the above and other objects are attained by an uneven texture-correcting cosmetic composition comprising (a) a partially crosslinked organopolysiloxane, (b) an oil-absorbing silicone composite spherical powder, and (c) 8 to 85% by weight of an oil having a viscosity of 1 to 100 mm$^2$/s at 25° C., wherein the total amount of components (a) and (b) is 10 to 35% by weight, and a weight ratio (a)/(b) of component (a) to component (b) is from 0.02 to 0.55. The invention is predicated on this finding.

Accordingly, the invention provides an uneven texture-correcting cosmetic composition as defined below.

[1] An uneven texture-correcting cosmetic composition comprising (a) a partially crosslinked organopolysiloxane, (b) an oil-absorbing silicone composite spherical powder, and (c) 8 to 85% by weight of an oil having a viscosity of 1 to 100 mm$^2$/s at 25° C., wherein the total amount of components (a) and (b) is 10 to 35% by weight, and a weight ratio (a)/(b) of component (a) to component (b) is from 0.02 to 0.55.

[2] The uneven texture-correcting cosmetic composition of [1], further comprising (d) a non-crosslinked silicone surfactant.

[3] The uneven texture-correcting cosmetic composition of [1] or [2], further comprising (e) a pigment having a refractive index of at least 1.8 (exclusive of component (b)).

[4] The uneven texture-correcting cosmetic composition of any one of [1] to [3], further comprising (f) a spherical powder other than components (b) and (e).

[5] The uneven texture-correcting cosmetic composition of any one of [1] to [4] wherein component (c) is a silicone oil.

[6] The uneven texture-correcting cosmetic composition of any one of [1] to [5] wherein component (b) is one or more members selected from (vinyl dimethicone/methicone silsesquioxane) crosspolymer, (diphenyl dimethicone/vinyldiphenyl dimethicone/silsesquioxane) crosspolymer, polysilicone-22, and polysilicone-1 crosspolymer, as defined by the nomenclature of cosmetic ingredients.

Advantageous Effects of Invention

According to the invention, there is provided a cosmetic composition featuring an uneven texture-correcting effect, feel-on-use, spreading or extension, and adhesion, and leaving no powder residues.

DESCRIPTION OF EMBODIMENTS

Now the invention is described in detail although the invention is not limited thereto.
[Component (a)]
Component (a) is a partially crosslinked organopolysiloxane, which is not particularly limited as long as it may be commonly formulated in cosmetics and which may be used alone or in admixture. Component (a) is an elastomer having silicone chains crosslinked with silicone and exhibiting a structural viscosity when swollen in oil. Specific examples include (dimethicone/vinyl dimethicone) crosspolymer and the like as defined by the nomenclature of cosmetic ingredients (INCI). These elastomers are commercially available as swollen products containing silicone oil or other oils and marketed under the trade name of KSG-15, 1510, 16, 15AP, and 19 (all from Shin-Etsu Chemical Co., Ltd.), for example.

Examples of the crosslinked product having alkyl branches on the main chain (alkyl-modified, partially crosslinked dimethylpolysiloxane, and silicone/alkyl-modified, partially crosslinked dimethylpolysiloxane), and the crosslinked product having a phenyl group in a crosslinked portion (phenyl-modified, partially crosslinked dimethylpolysiloxane) include (vinyl dimethicone/lauryl dimethicone) crosspolymer, (lauryl polydimethylsiloxyethyl dimethicone/bisvinyl dimethicone) crosspolymer, and (dimethicone/phenyl vinyl dimethicone) crosspolymer as defined by INCI. They are commercially available as swollen products containing normally liquid oil and marketed under the trade name of KSG-18A, 41A, 42A, 43, 44, 042Z, 045Z, 048Z, and 18A (all from Shin-Etsu Chemical Co., Ltd.), for example.

The amount of component (a) formulated is preferably 0.2 to 12.4% by weight, more preferably 0.35 to 10.3% by weight, even more preferably 0.58 to 9.3% by weight of the overall uneven texture-correcting cosmetic composition. Less than 0.2 wt % of component (a) may fail to provide sufficient adhesion and rich feeling whereas more than 12.4 wt % may fail to provide an adequate coating thickness.

[Component (b)]

Component (b) is an oil-absorbing silicone composite spherical particle powder, which is not particularly limited as long as it may be commonly formulated in cosmetics and which may be used alone or in admixture. As used herein, the oil-absorbing powder is a powder having an oil absorption of at least 70 mL/100 g, preferably at least 100 mL/100 g, as measured by the test method of JIS K5101 in which linseed oil is replaced by silicone oil having a viscosity of 1 to 20 mm$^2$/s at 25° C. (specifically, KF-96A-6cs or KF-56A, both available from Shin-Etsu Chemical Co., Ltd.). If a composition is heavily loaded with a powder having an oil absorption of less than 70 mL/100 g, white residues are sometimes found.

The spherical powder particles refer to particles of spherical shape having a nearly spherical diameter and may be spherical particles having uneven surface, specifically spherical particles having a breadth/length ratio of preferably up to 1.5, more preferably up to 1.2, even more preferably up to 1.1. Component (b) is a composite spherical powder having such spherical particles covered with spherical particles of different type.

Of these oil-absorbing silicone composite spherical particle powders, silicone resin-coated silicone rubber particle powders are preferred from the standpoints of an effect of improving feel, typically providing an anti-sticky feel and an effect of correcting skin texture defects such as wrinkles and pores. Examples of the silicone resin-coated silicone rubber particle powder, also referred to as hybrid silicone powder, include (vinyl dimethicone/methicone silsesquioxane) crosspolymer, (diphenyl dimethicone/vinyl diphenyl dimethicone/silsesquioxane) crosspolymer, polysilicone-22, and polysilicone-1 crosspolymer, as defined by the INCI. They are commercially available under the trade name of KSP-100, 101, 102 105, 300, 411 and 441 (all from Shin-Etsu Chemical Co., Ltd.).

The amount of component (b) formulated is preferably 6.5 to 34.3% by weight, more preferably 8 to 30% by weight, even more preferably 10.4 to 28.8% by weight of the overall uneven texture-correcting cosmetic composition. Less than 6.5 wt % of component (b) may fail to provide a sufficient uneven texture-correcting effect whereas more than 34.3 wt % may leave powder residues.

In the practice of the invention, the total amount of components (a) and (b) formulated is 10 to 35% by weight, preferably 12 to 31% by weight, more preferably 15 to 30% by weight of the overall uneven texture-correcting cosmetic composition. Less than 10 wt % of components (a)+(b) fails to provide a satisfactory uneven texture-correcting effect whereas more than 35 wt % causes a strong film feeling and a powdery feeling. Also the weight ratio (a)/(b) of component (a) to component (b) is 0.02 to 0.55, preferably 0.03 to 0.50, more preferably 0.04 to 0.45. If the weight ratio is less than 0.02, there arise problems such as a strong powdery feeling, poor spread, powder residues and inefficient finger pickup. If the weight ratio is more than 0.55, there arise undesirable problems such as a strong gel feeling or oily feeling, increased cosmetic film thickness, and unnatural finish.

[Component (c)]

Component (c) is an oil having a viscosity of 1 to 100 mm$^2$/s at 25° C., which is not particularly limited as long as it is a raw material commonly formulated in cosmetics. Examples of the oil used herein include silicone oils, hydrocarbon oils, ester oils, UV absorbers, and fluorinated oils, which may be used alone or in a suitable combination of two or more.

Silicone Oil

The silicone oil is not particularly limited as long as it is a raw material commonly formulated in cosmetics. Examples include dimethylpolysiloxane, cyclopentasiloxane (decamethylcyclopentasiloxane), cyclohexasiloxane, disiloxane, trisiloxane, methyl trimethicone, caprylylmethicone, diphenyl dimethicone (dimethicone/vinyl dimethicone) crosspolymer, diphenylsiloxyphenyl trimethicone (INCI name), methylphenylpolysiloxane, methylhexylpolysiloxane, methylhydrogenpolysiloxane, and dimethylsiloxane-methylphenylsiloxane copolymers. Of these, preference is given to volatile silicones providing a fresh feel-on-use (commercially available as TMF-1.5, KF-995, KF-96A-1cs, KF-96A-1.5cs, KF-96A-2cs from Shin-Etsu Chemical Co., Ltd.), low-viscosity silicones (commercially available as KF-96A-6cs from Shin-Etsu Chemical Co., Ltd.), and phenyl silicones used for the purposes of improving compatibility with other oils and lustering (commercially available as KF-56A from Shin-Etsu Chemical Co., Ltd.). These silicone oils may be used alone or in admixture.

Suitable other oils include cetyl ethylhexanoate, triethylhexanoin, tri(caprylic acid/capric acid) glyceryl, isononyl isononanoate, isotridecyl isononanoate, isopropyl palmitate, dicaprylyl ether, isopropyl myristate, ethylhexyl palmitate, diethylhexyl carbonate, dicaprylyl carbonate, C$_{12-15}$ alkyl benzoates, neopentylglycol diethylhexanoate, isododecane, undecane, 2-ethylhexyl p-methoxycinnamate, and octyl salicylate.

Component (c) has a viscosity at 25° C. of 1 to 100 mm$^2$/s (also expressed cSt or cs), preferably 1 to 50 mm$^2$/s, more preferably 1 to 30 mm$^2$/s. Heavy loading of an oil having a viscosity of less than 1 mm$^2$/s may lead to irritation whereas heavy loading of an oil having a viscosity of more than 100 mm$^2$/s may adversely affect the oil absorption ability of the oil-absorbing powder. It is noted that the kinematic viscosity is measured at 25° C. by an Ostwald viscometer.

The amount of component (c) formulated is 8 to 85% by weight, preferably 12 to 73% by weight, more preferably 15 to 65% by weight of the overall uneven texture-correcting cosmetic composition. Less than 8 wt % of component (c) leads to unfavorable spread whereas more than 85 wt % gives a strong oily feeling.

The weight ratio (b)/(c) of component (b) to component (c) is preferably 0.1 to 0.6, more preferably 0.15 to 0.6, even more preferably 0.2 to 0.6. With a weight ratio (b)/(c) of at least 0.1, a satisfactory uneven texture-correcting effect is exerted. With a weight ratio of up to 0.6, a powdery feeling is suppressed.

[Component (d)]

In the uneven texture-correcting cosmetic composition, (d) a non-crosslinked silicone surfactant is preferably formulated from the standpoints of adjustment of the wettability of component (b), adjustment of a feel-on-use, ease of coating and finger pickup, and preparation storage stability. The non-crosslinked silicone surfactant is not particularly limited as long as it is an ingredient commonly formulated in cosmetics, while it may be used alone or in a suitable combination of two or more. Preferred surfactants include polyether-modified silicones such as linear or branched polyoxyethylene-modified organopolysiloxane, linear or branched polyoxyethylenepolyoxypropylene-modified organopolysiloxane, linear or branched polyoxyethylene/alkyl-co-modified organopolysiloxane, linear or branched polyoxyethylenepolyoxypropylene/alkyl-co-modified organopolysiloxane; and polyglycerin-modified silicones such as linear or branched polyglycerin-modified organopolysiloxane, linear or branched polyglycerin/alkyl-co-modified organopolysiloxane. Specific examples include KF-6011, 6013, 6043, 6017, 6028, 6038, 6048, 6100, 6104, 6105, and 6106. Of these, branched silicones KF-6028, 6038, 6100, 6104, 6105 and 6106 are preferred in view of a feel-on-use. These non-crosslinked silicone surfactants may be used alone or in admixture.

When component (d) is used, the amount of component (d) formulated is preferably 0.1 to 5% by weight, more preferably 0.2 to 4% by weight of the overall uneven texture-correcting cosmetic composition. At least 0.1 wt % of component (d) leads to more improvements in coating and finger pickup of the cosmetic composition whereas up to 5 wt % ensures a good feeling on application.

[Component (e)]

In the uneven texture-correcting cosmetic composition, (e) a pigment having a refractive index of at least 1.8 (exclusive of component (b)) is preferably formulated from the standpoint of adjustment of covering power. The pigment used herein is not particularly limited as long as it is a pigment having a refractive index of at least 1.8 commonly formulated in cosmetics, while it may be used alone or in admixture.

Examples of the pigment having a refractive index of at least 1.8 include inorganic pigments such as zinc white, titanium dioxide, red iron oxide, yellow iron oxide, black iron oxide, titanium sub-oxide, chromium oxide, chromium hydroxide, and bismuth oxychloride. Pigments hydrophobized with silicone are also useful. Examples of the hydrophobized inorganic powder include those commercially available as dispersions containing hydrophobized microparticulate titanium oxide and hydrophobized microparticulate zinc oxide, which are marketed under the trade name of SPD-T5, T6, TSL, Z5, Z6 and Z5L (all from Shin-Etsu Chemical Co., Ltd.).

When component (e) is used, the amount of component (e) formulated is preferably 0.1 to 60% by weight of the overall uneven texture-correcting cosmetic composition, and in view of ease of use, more preferably 1 to 20% by weight. Less than 0.1 wt % of component (e) fails to obtain a satisfactory covering effect and coloring effect whereas more than 60 wt % of component (e) adversely affects spread on use and causes a cosmetic film to be powdery.

[Component (f)]

In the uneven texture-correcting cosmetic composition, a spherical particle powder other than components (b) and (e) is preferably formulated as a coagent for adjusting a feel-on-use and augmenting an uneven texture-correcting effect. Component (f) is not particularly limited as long as it is a spherical particle powder commonly formulated in cosmetics. Examples include silicone spherical particle powder, polyamide powder, polyurethane powder, polymethacrylate, and polyacrylate while the powder may be used alone or in a suitable combination of two or more.

Silicone Spherical Particle Powder

Included are crosslinked silicone powder (i.e., so-called silicone rubber powder consisting of organopolysiloxane of the structure having repeating chains of diorganosiloxane units crosslinked), and silicone resin particles, for example, spherical polyorganosilsesquioxane (polyorganosilsesquioxane resin particles of three-dimensional network structure). Examples are known under the INCI name of (dimethicone/vinyl dimethicone) crosspolymer and polymethylsilsesquioxane. They are commercially available in powder form or swollen form containing silicone oil, and marketed, for example, under the trade name of KMP-598, 590, 591, and KSG-016F (all from Shin-Etsu Chemical Co., Ltd.).

[Other Optional Components]

Various components which are used in ordinary cosmetics may be formulated in the cosmetic composition of the invention as long as the benefits of the invention are not impaired. Suitable components include, for example, (1) an oil other than component (c), (2) an aqueous component, (3) a film-forming agent, (4) a surfactant other than component (d), (5) a UV absorber other than component (c), (6) a wax, (7) a powder other than components (b), (e) and (f), and (8) other additives. These components may be used alone or in a suitable combination of two or more.

(1) Oil Other Than Component (c)

The oil other than component (c) used herein is not particularly limited as long as it is a raw material commonly formulated in cosmetics for touch adjustment and emollient effect. Examples include high-viscosity linear or branched organopolysiloxane, amino-modified organopolysiloxane, pyrrolidone-modified organopolysiloxane, pyrrolidone carboxylate-modified organopolysiloxane, gum-like dimethylpolysiloxane having a high degree of polymerization, gum-like amino-modified organopolysiloxane, and cyclic organopolysiloxane solutions such as silicone gum, higher alkoxy-modified silicones such as stearoxysilicone, higher fatty acid-modified silicones, alkyl-modified silicones, long-chain alkyl-modified silicones, amino acid-modified silicones, fluorine-modified silicones, silicone resins, and dissolved silicone resins. Of these, preference is given to silicone waxes, which are commonly used for the purpose of lustering or adjusting feel-on-use and commercially available as KP-561P, 562P, and KF-7020S from Shin-Etsu Chemical Co., Ltd. Besides the silicones, high-viscosity hydrocarbon oils such as vaseline and hydrogenated polyisobutene are also useful. When used, the oil other than component (c) is preferably blended in an amount of 0.1 to 20% by weight of the overall uneven texture-correcting cosmetic composition.

(2) Aqueous Component

The aqueous component is not particularly limited as long as it is a raw material commonly blended in cosmetics for the purpose of exerting a humectant or refreshing effect. Examples include lower alcohols such as ethanol and isopropanol; sucrose alcohols such as sorbitol, maltose and xylitol; polyhydric alcohols such as butylene glycol, dibutylene glycol, propylene glycol, dibutylene glycol, pentylene glycol, decanediol, octanediol, hexanediol, erythritol, glycerin, diglycerin, and polyethylene glycol; glucose, glyceryl glucoxide, betaine, hyaluronic acid, chondroitin sulfate, pyrrolidone carboxylate, polyoxyethylene methyl glucoxide, and polyoxypropylene methyl glucoxide. When used, the aqueous component is preferably blended in an amount of 0.1 to 30% by weight based on the overall uneven texture-correcting cosmetic composition.

(3) Film-Forming Agent

The film-forming agent used herein is not particularly limited as long as it is a raw material commonly used in cosmetics. Examples include latexes such as polyvinyl alcohol, polyvinyl pyrrolidone, polyvinyl acetate, polyalkyl acrylates; cellulose derivatives such as dextrin, alkyl celluloses, and nitrocellulose; silicone-modified polysaccharides such as pullulan tri(trimethylsiloxy)silylpropylcarbamate, acrylic silicone base graft copolymers such as (alkyl acrylate/dimethicone) copolymers, silicone resins such as trimethylsiloxysilicic acid, silicone base resins such as silicone-modified polynorbornene and fluorine-modified silicone resins, fluoro-resins, aromatic hydrocarbon resins, polymer emulsion resins, terpene resins, polybutene, polyisoprene, alkyd resins, polyvinyl pyrrolidone-modified polymers, rosin-modified resins, and polyurethane. When used, the film-forming agent is preferably blended in an amount of 0.1 to 20% by weight based on the overall uneven texture-correcting cosmetic composition.

Among these, silicone base film-forming agents are preferred. More preferred examples include, but are not limited to, pullulan tri(trimethylsiloxy)silylpropylcarbamate (commercially available in solvent solution form as TSPL-30-D5, ID from Shin-Etsu Chemical Co., Ltd.), (alkyl acrylate/dimethicone) copolymers (commercially available in solvent solution form as KP-543, 545, 549, 550, 545L from Shin-Etsu Chemical Co., Ltd.), trimethylsiloxysilicic acid (commercially available in solvent solution form as KF-7312J, X-21-5250 from Shin-Etsu Chemical Co., Ltd.), and silicone-modified polynorbornene (commercially available in solvent solution form as NBN-30-ID from Shin-Etsu Chemical Co., Ltd.). The film-forming agent may be used alone or in admixture.

(4) Surfactant Other Than Component (d)

The surfactant other than component (d) used herein is not particularly limited as long as it is commonly used in cosmetics. While suitable surfactants include nonionic, anionic, cationic and ampholytic surfactants, any of these may be used. Of the surfactants, partially crosslinked polyether-modified silicones and partially crosslinked polyglycerin-modified silicones are preferred. Unlike component (a) defined above, these are compounds of the structure that silicone chains are crosslinked with polyether or polyglycerin, and examples include (dimethicone/(PEG-10/15)) crosspolymer, (PEG-15/lauryl dimethicone) crosspolymer, (PEG-15/lauryl polydimethylsiloxyethyl dimethicone) crosspolymer, (dimethicone/polyglycerin-3) crosspolymer, (lauryl dimethicone/polyglycerin-3) crosspolymer, (polyglyceryl-3/lauryl polydimethylsiloxyethyl dimethicone) crosspolymer, in INCI name. They are commercially available as swollen products containing silicone oils or other oils and marketed, for example, under the tradename of KSG-210, 240, 310, 340, 320Z, KSG-710, 810, 820Z (all from Shin-Etsu Chemical Co., Ltd.). They may be used alone or in a suitable combination of two or more. In a combination of partially crosslinked polyether-modified silicone with partially crosslinked polyglycerin-modified silicone, for example, there is a tendency that the cosmetic composition becomes more spreadable as the relative proportion of partially crosslinked polyether-modified silicone is high, and there is a tendency that the cosmetic composition gives a more moist, soft feel-on-use as the relative proportion of partially crosslinked polyglycerin-modified silicone is high. The blending proportion of these silicones may be determined as appropriate for proper control of a feel-on-use.

(5) UV Absorber Other Than Component (c)

The UV absorber other than component (c) used herein is not particularly limited as long as it is a raw material commonly blended in cosmetics. Examples include homomenthyl salicylate, octocrylene, 4-tert-butyl-4'-methoxydibenzoylmethane, 4-(2-β-glucopyranosiloxy) propoxy-2-hydroxybenzophenone, hexyl 2-[4-(diethylamino)-2-hydroxybenzoyl]benzoate, dihydroxydimethoxybenzophenone, sodium dihydroxydimethoxybenzophenonedisulfonate, dihydroxybenzophenone, dimethicodiethylbenzal malonate, 1-(3,4-dimethoxyphenyl)-4,4-dimethyl-1,3-pentanedione, 2-ethylhexyl dimethoxybenzylidenedioxoimidazolidinepropionate, tetrahydroxybenzophenone, terephthalylidene dicamphor sulfonic acid, 2,4,6-tris[4-(2-ethylhexyloxycarbonyl)anilino]-1,3,5-triazine, methylbis(trimethylsiloxy)silylisopentyl trimethoxycinnamate, drometrizole trisiloxane, 2-ethylhexyl p-dimethylaminobenzoate, isopropyl p-methoxycinnamate, 2,4-bis[{4-(2-ethylhexyloxy)-2-hydroxy}-phenyl]-6-(4-methoxyphenyl)-1,3,5-triazine, 2-hydroxy-4-methoxybenzophenone, hydroxymethoxybenzophenone sulfonic acid and trihydrate thereof, sodium hydroxymethoxybenzophenone sulfonate, phenylbenzimidazole sulfonic acid, and 2,2'-methylenebis(6-(2H-benzotriazol-2-yl)-4-(1,1,3,3-tetramethylbutyl)phenol). Also, a UVA absorber (e.g., hexyl diethylaminohydroxybenzoylbenzoate) may be combined with a UVB absorber (e.g., octocrylene) or the UV absorber as component (c). Any two or more of the foregoing may be used in combination.

(6) Wax

The wax used herein is not particularly limited as long as it is a raw material commonly used in cosmetics and capable of solidifying the oil. Suitable waxes include hydrocarbon waxes such as ceresin, ozokerite, paraffin, synthetic wax, microcrystalline wax, polyethylene wax; plant-derived waxes such as carnauba wax, rice wax, rice bran wax, jojoba wax (inclusive of extremely hydrogenated jojoba oil), candelilla wax; and animal-derived waxes such as whale wax, bee wax and insect wax, which may be used alone or in admixture. When used, the amount of the wax blended is preferably 0.1 to 10% by weight based on the uneven texture-correcting cosmetic composition.

(7) Powder Other Than Components (b), (e) and (f)

The other powder used herein is not particularly limited as long as it is a raw material commonly used in cosmetics. Examples include mica, talc, sericite, barium sulfate, calcium carbonate, and kaolin.

(8) Other Additives

Other additives include water, oil-soluble gelling agents, antiperspirants, humectants, bactericides, preservatives, perfumes, salts, antioxidants, pH adjusting agents, chelating agents, refreshing agents, anti-inflammatory agents, skin improving agents (brightening agent, cell activating agent, anti-skin-roughening agent, blood flow promotor, skin astringent, antiseborrheic agent), vitamins, amino acids, water-soluble polymers, and plant extracts.

Oil-Soluble Gelling Agent

Suitable oil-soluble gelling agents include metal soaps such as aluminum stearate, magnesium stearate, and zinc myristate; amino acid derivatives such as N-lauroyl-L-glutamic acid and α,γ-di-n-butylamine; dextrin fatty acid esters such as dextrin palmitate, dextrin stearate, and dextrin 2-ethylhexanate palmitate; sucrose fatty acid esters such as sucrose palmitate and sucrose stearate; fructooligosaccharide fatty acid esters such as fructooligosaccharide stearate and fructooligosaccharide 2-ethylhexanoate; benzylidene derivatives of sorbitol such as monobenzylidene sorbitol and dibenzylidene sorbitol; and organo-modified clay minerals such as disteardimonium hectorite, stearalkonium hectorite and hectorite.

Preservative and Bactericide

Examples of the preservative and bactericide include alkyl p-hydroxybenzoates, benzoic acid, sodium benzoate, sorbic acid, potassium sorbate, phenoxyethanol, imidazolidinium urea, benzoic acid, salicylic acid, isopropyl methyl phenol, carbolic acid, alkyl p-hydroxybenzoates, p-chloro-m-cresol, hexachlorophene, benzalkonium chloride, chlorohexidine chloride, trichlorocarbaniride, iodopropinyl butylcarbamate, polylysine, photosensitizer, and silver.

[Preparation Method]

The cosmetic composition of the invention may be prepared by any well-known methods. It is not critical how to mix components (a) and (b). Components (a) and (b) may be used by previously mixing them with the oil other than components (c) and (d), previously emulsifying them in water to form an emulsion, or treating them to be hydrophilic so that they are readily formulated in an aqueous system.

[Uneven Texture-Correcting Cosmetic Composition]

As used herein, the term "uneven texture-correcting" refers to shading or smoothening pores, wrinkles or furrows for rendering uneven skin texture less perceivable. The cosmetic composition may be of emulsion or non-aqueous form. The emulsion composition is selected when a fresh feel-on-use is desired. The emulsion form may be any of O/W, W/O, and W/O/W types. The non-aqueous composition or powder form is selected when unctuous feeling, water resistance or powdery feeling is desired. In either form, a satisfactory cosmetic composition is obtained. As used herein, the term "non-aqueous composition" refers to an oily composition substantially free of water.

The type of the uneven texture-correcting cosmetic composition is not particularly limited as long as it contains essential ingredients. For example, the cosmetic composition may be implemented as toilet water, lotion, milky lotion, cream, hair care, foundation, foundation primer, BB cream, concealer, sunscreen, loose powder, cheek color, lipstick, eyeshadow, eyeliner, body makeup, deodorant, etc. Of these, foundation, foundation primer, BB cream, concealer, and cheek color are preferred in that the benefits of the invention are fully obtained. The cosmetic composition may take a variety of formulas including liquid, cream, solid, paste, gel, mousse, souffle, clay, powder, etc.

EXAMPLES

Examples and Comparative Examples are shown below for further illustrating the invention although the invention is not limited thereto. In Examples, steps are carried out at room temperature unless otherwise stated, and compositional percent (%) and ratio are by weight.

EXAMPLES AND COMPARATIVE EXAMPLES

Cosmetic compositions of the formulation shown in Tables were prepared and evaluated by the following methods.

Preparation of Cosmetic Compositions: Examples 1 to 10 and Comparative Examples 1 to 9

A non-aqueous concealer was prepared by mixing components until uniform.

Preparation of Cosmetic Compositions: Examples 11 to 13 and Comparative Examples 10 to 12

A water-in-oil type concealer was prepared by step A of mixing component (2) on a three-roll mill until uniform, step B of adding A to component or mixture (1) and mixing them until uniform, and step C of adding component (3) to B and emulsifying them.

(1) Evaluation of Properties

The cosmetic compositions of Examples and Comparative Examples were evaluated for uneven texture correction (rendering pores and wrinkles unperceivable), feel-on-use (free of unctuous feel), spread (or extensibility), powder residues (free of white masking or powdery feel), and adhesion (ease of finger pickup or skin adhesion) by a panel of 10 members. Evaluation was made in accordance with the criteria shown in Table 1. The result is an average of ratings of 10 panel members and rated according to the judgment criteria shown below. The results are shown in Tables 2 to 4.

TABLE 1

| Point | Uneven texture correction | Feel-on-use | Spread | Powder residues | Adhesion |
|---|---|---|---|---|---|
| 5 | good | good | good | good | good |
| 4 | rather good | rather good | rather good | rather good | rather good |
| 3 | ordinary | ordinary | ordinary | ordinary | ordinary |
| 2 | rather bad | rather bad | rather bad | rather bad | rather bad |
| 1 | bad | bad | bad | bad | bad |

(2) Judgment Criteria

⊚: average point≥4.5
○: 3.5 average point<4.5
Δ: 2.5 average point<3.5
x: 1.5 average point<2.5
xx: average point<1.5

TABLE 2

| Component (%) | Example |  |  |  |  |  |  |  |  |  |
|---|---|---|---|---|---|---|---|---|---|---|
|  | 1 | 2 | 3 | 4 | 5 | 6 | 7 | 8 | 9 | 10 |
| (a) Partially crosslinked dimethylpolysiloxane (25%) dimethicone mixture *1 | 6 | 6 | 2 | 3 | 19 | 8 | 8 | 8 | 8 | 8 |
| (b) Silicone composite powder A *2 | 25.5 | 25.5 | 25 | 25 | 9.5 | 8 | 10 | 8 | 8 | 8 |
| (d) Polyether-modified silicone *3 |  | 0.5 | 0.5 |  0.5 |  |  |  |  |  |  |
| (f) Spherical polymethylsilsesquioxane *4 |  |  |  |  |  |  |  | 2 |  |  |
| (f) Spherical poly(methyl methacrylate) (8 μm) |  |  |  |  |  |  |  |  | 2 |  |
| (e) Titanium oxide |  |  |  |  |  |  |  |  |  | 2 |
| Hydrophilic anhydrous silica *5 |  |  | 2 | 2 | 5 | 5 | 5 | 5 | 5 | 5 |
| (c) Dimethylpolysiloxane (6 cs) | 68.5 | 68.0 | 70.5 | 69.5 | 66.5 | 79.0 | 77.0 | 77.0 | 77.0 | 77.0 |
| Total | 100 | 100 | 100 | 100 | 100 | 100 | 100 | 100 | 100 | 100 |

TABLE 2-continued

| Component (%) | Example | | | | | | | | | |
|---|---|---|---|---|---|---|---|---|---|---|
| | 1 | 2 | 3 | 4 | 5 | 6 | 7 | 8 | 9 | 10 |
| (a) + (b) | 27 | 27 | 25.5 | 25.5 | 14.25 | 10 | 12 | 10 | 10 | 10 |
| (a)/(b) | 0.06 | 0.06 | 0.02 | 0.03 | 0.50 | 0.25 | 0.20 | 0.25 | 0.25 | 0.25 |
| (b)/(c) | 0.3 | 0.4 | 0.3 | 0.3 | 0.1 | 0.1 | 0.1 | 0.1 | 0.1 | 0.1 |
| Uneven texture correction | ◉ | ◉ | ◉ | ◉ | ○ | Δ | ○ | ○ | ○ | ○ |
| Feel-on-use | ◉ | ◉ | ○ | ○ | ○ | ○ | ◉ | ◉ | ○ | Δ |
| Spread | ◉ | ◉ | ○ | ○ | ○ | ◉ | ◉ | ◉ | ◉ | ◉ |
| Powder residues | ○ | ◉ | Δ | ○ | ◉ | ◉ | ◉ | ◉ | ○ | ○ |
| Adhesion | ○ | ◉ | ◉ | ◉ | ◉ | ○ | ○ | ○ | ○ | ○ |

*1 (dimethicone/vinyl dimethicone) crosspolymer: KSG-16 (crosslink 25%, dimethylpolysiloxane (6 cs) 75%) by Shin-Etsu Chemical Co., Ltd.
*2 (vinyl dimethicone/methicone silsesquioxane) crosspolymer: KSP-101 by Shin-Etsu Chemical Co., Ltd.
*3 PEG-10 dimethicone: KF-6017 by Shin-Etsu Chemical Co., Ltd.
*4 KMP-591 by Shin-Etsu Chemical Co., Ltd.
*5 Aerosil 200 by Nippon Aerosil Co., Ltd.

Each blend amount is the amount of the designated product blended whereas (a)+(b), (a)/(b), and (b)/(c) are based on net amounts (the same holds true, hereinafter).

TABLE 3

| Component (%) | Comparative Example | | | | | | | | |
|---|---|---|---|---|---|---|---|---|---|
| | 1 | 2 | 3 | 4 | 5 | 6 | 7 | 8 | 9 |
| (a) Partially crosslinked dimethylpolysiloxane (25%) dimethicone mixture *1 | | | 20 | 40 | 16 | 7 | 8 | 8 | 8 |
| (b) Silicone composite powder A *2 | 25.5 | 25.5 | | | 6 | 7 | | | |
| (f) Spherical polymethylsilsesquioxane *4 | | | | | | | 10 | | |
| (f) Spherical poly(methyl methacrylate) (8 μm) | | | | | | | | 10 | |
| (e) Titanium oxide | | | | | | | | | 10 |
| Hydrophilic anhydrous silica *5 | | | 10 | 5 | 5 | 5 | 5 | 5 | 5 |
| Highly polymerized dimethylpolysiloxane (100,000 cs) | | 20 | | | | | | | |
| (c) Dimethylpolysiloxane (6 cs) | 74.5 | 54.5 | 70.0 | 55.0 | 73.0 | 81.0 | 77.0 | 77.0 | 77.0 |
| Total | 100 | 100 | 100 | 100 | 100 | 100 | 100 | 100 | 100 |
| (a) + (b) | 25.5 | 25.5 | 5 | 10 | 10 | 8.75 | — | — | — |
| (a)/(b) | — | — | — | — | 0.67 | 0.25 | — | — | — |
| Uneven texture correction | ◉ | ◉ | Δ | Δ | Δ | Δ | Δ | Δ | X |
| Feel-on-use | ○ | XX | XX | XX | X | X | X | X | XX |
| Spread | X | X | Δ | Δ | Δ | ○ | ○ | ○ | X |
| Powder residues | XX | X | ◉ | ◉ | ◉ | ○ | ○ | ○ | ○ |
| Adhesion | X | Δ | Δ | Δ | Δ | ○ | ○ | ○ | ○ |

*1 (dimethicone/vinyl dimethicone) crosspolymer: KSG-16 (crosslink 25%, dimethylpolysiloxane (6 cs) 75%) by Shin-Etsu Chemical Co., Ltd.
*2 (vinyl dimethicone/methicone silsesquioxane) crosspolymer: KSP-101 by Shin-Etsu Chemical Co., Ltd.
*3 PEG-10 dimethicone: KF-6017 by Shin-Etsu Chemical Co., Ltd.
*4 KMP-591 by Shin-Etsu Chemical Co., Ltd.
*5 Aerosil 200 by Nippon Aerosil Co., Ltd.

TABLE 4

| Component (%) | Example | | | | Comparative Example | |
|---|---|---|---|---|---|---|
| | 11 | 12 | 13 | 10 | 11 | 12 |
| (1) (a) Partially crosslinked dimethylpolysiloxane (25%) composition *1 | 5 | 16 | | 16 | | |
| (a) Phenyl-modified partially crosslinked dimethylpolysiloxane (15%) composition *2 | 5 | | 30 | 2 | 2 | 30 |
| (b) Silicone composite powder B *3 | 5 | 5 | 5 | 5 | 15 | 5 |
| (b) Phenyl-modified silicone composite powder *4 | 5 | 5 | 5 | 2 | 5 | |
| Trimethylsiloxysilicic acid composition *5 | 3 | 3 | 3 | 3 | 3 | 3 |
| (c) Diphenylsiloxyphenyl dimethicone *6 | 5 | 5 | 5 | 5 | 5 | 5 |
| (c) Decamethylcyclopentasiloxane | 20 | 20 | 20 | 20 | 20 | 20 |
| (c) Ethylhexyl methoxycinnamate | 3 | 3 | 3 | 3 | 3 | 3 |
| (d) Alkyl/silicone branched polyether-modified silicone *7 | 3 | 3 | 3 | 3 | 3 | 3 |
| Disteardimonium hectorite | 1 | 1 | 1 | 1 | 1 | 1 |

TABLE 4-continued

|  | Example | | | | Comparative Example | |
| --- | --- | --- | --- | --- | --- | --- |
| Component (%) | 11 | 12 | 13 | 10 | 11 | 12 |
| (2) (c) Isotridecyl isononanoate | 4 | 4 | 4 | 4 | 4 | 4 |
| (d) Silicone branched polyether-modified silicone *8 | 1 | 1 | 1 | 1 | 1 | 1 |
| (e) Silicone-treated titanium oxide *9 | 8.5 | 8.5 | 8.5 | 8.5 | 8.5 | 8.5 |
| (e) Silicone-treated iron oxide *9 | 1.5 | 1.5 | 1.5 | 1.5 | 1.5 | 1.5 |
| Silicone-treated talc *9 | 2 | 2 | 2 | 2 | 2 | 2 |
| (3) Butylene glycol | 5 | 5 | 5 | 5 | 5 | 5 |
| Sodium chloride | 0.5 | 0.5 | 0.5 | 0.5 | 0.5 | 0.5 |
| Purified water | balance | balance | balance | balance | balance | balance |
| Total | 100 | 100 | 100 | 100 | 100 | 100 |
| (a) + (b) | 12 | 14 | 14.5 | 11.3 | 20.3 | 9.5 |
| (a)/(b) | 0.20 | 0.40 | 0.45 | 0.61 | 0.015 | 0.90 |
| (b)/(c) | 0.3 | 0.2 | 0.2 |  |  |  |
| Uneven texture correction | ⊚ | ⊚ | ⊚ | ⊚ | ⊚ | ◯ |
| Feel-on-use | ⊚ | ◯ | ◯ | X | ⊚ | XX |
| Spread | ⊚ | ⊚ | ⊚ | ◯ | X | ◯ |
| Powder residues | ⊚ | ⊚ | ⊚ | ⊚ | XX | ⊚ |
| Adhesion | ◯ | ⊚ | ⊚ | ◯ | ◯ | ◯ |

*1 (dimethicone/vinyl dimethicone) crosspolymer: KSG-16 (crosslink 25%, dimethylpolysiloxane (6 cs) 75%) by Shin-Etsu Chemical Co., Ltd.
*2 (dimethicone/phenylvinyl dimethicone) crosspolymer: KSG-18A (crosslink 15%, dimethylpolysiloxane (6 cs) 75%) by Shin-Etsu Chemical Co., Ltd.
*3 (vinyl dimethicone/methicone silsesquioxane) crosspolymer: KSP-100 by Shin-Etsu Chemical Co., Ltd.
*4 (diphenyl dimethicone/vinyldiphenyl dimethicone/silsesquioxane) crosspolymer: KSP-300 by Shin-Etsu Chemical Co., Ltd.
*5 KF-9021 (solids 50%, decamethylcyclopentasiloxane 50%) by Shin-Etsu Chemical Co., Ltd.
*6 trimethylsiloxycinnamic acid: KF-56A by Shin-Etsu Chemical Co., Ltd.
*7 lauryl PEG-9 polydimethylsiloxyethyl dimethicone: KF-6038 by Shin-Etsu Chemical Co., Ltd.
*8 PEG-9 polydimethylsiloxyethyl dimethicone: KF-6028 by Shin-Etsu Chemical Co., Ltd.
*9 hydrophobic powder surface-treated with KF-9901 by Shin-Etsu Chemical Co., Ltd.

As is evident from the results in Tables 2 to 4, the uneven texture-correcting cosmetic compositions of Examples 1 to 13 are excellent in uneven texture correction (rendering pores and wrinkles unperceivable), feel-on-use (free of unctuous feel), spread (good extensibility), powder residues (free of white masking or powdery feel), and adhesion (ease of finger pickup or skin adhesion). Comparative Examples 1 and 2 not using component (a), and Comparative Example 11 having a weight ratio (a)/(b) of less than 0.02 are unacceptable in any of spread, powder residues and adhesion. Comparative Examples 3 and 4 not using component (b), and Comparative Examples 7 to 9 using a different spherical powder or pigment as component (b) are unacceptable because of strong unctuous feel, poor spread, and insufficient uneven texture correction. Comparative Examples 5, 10 and 12 having a weight ratio (a)/(b) of more than 0.55 and Comparative Example 6 having a total content (a)+(b) of less than 10% give a strong unctuous feel and insufficient uneven texture correction.

Example 14

Concealer

<Preparation of Cosmetic Composition>

A concealer was prepared by step A of mixing ingredients (1) to (6) until uniform, step B of mixing ingredients (7) to (9) until uniform, and step C of mixing A and B until uniform.

| Formulation | % |
| --- | --- |
| (1) Partially crosslinked dimethylpolysiloxane composition *1 | 6 |
| (2) Diphenylsiloxyphenyl dimethicone *2 | 7 |
| (3) Dimethylpolysiloxane (6 cs) | balance |
| (4) Silicone branched polyether-modified silicone *3 | 0.5 |
| (5) Hybrid silicone composite powder *4 | 23.5 |
| (6) Phenyl-modified hybrid silicone composite powder *5 | 4.6 |

-continued

| Formulation | % |
| --- | --- |
| (7) Triethylhexanoin | 0.2 |
| (8) Silicone-treated titanium oxide *6 | 0.2 |
| (9) Silicone-treated iron oxide *6 | 0.1 |
| Total | 100.0 |

*1 (modified) partially crosslinked dimethylpolysiloxane composition: KSG-19 (crosslink 15%, dimethylpolysiloxane (6 cs) 85%) by Shin-Etsu Chemical Co., Ltd.
*2 diphenylsiloxyphenyl dimethicone: KF-56A by Shin-Etsu Chemical Co., Ltd.
*3 silicone branched polyether-modified silicone: KF-6028 by Shin-Etsu Chemical Co., Ltd.
*4 hybrid silicone composite powder: KSP-101 by Shin-Etsu Chemical Co., Ltd.
*5 phenyl-modified hybrid silicone composite powder: KSP-300 by Shin-Etsu Chemical Co., Ltd.
*6 hydrophobic powder surface-treated with KF-9909 by Shin-Etsu Chemical Co., Ltd.
total of components (a) and (b) = 29.9
(a)/(b) = 0.03

It was found that the resulting concealer was excellent in uneven texture correction, feel-on-use, spread, and adhesion, left no powder residues, and gave a natural finish.

Example 15

W/O Primer Cream

<Preparation of Cosmetic Composition>

A W/O primer cream was prepared by step A of mixing ingredients (1) to (9) until uniform, step B of mixing ingredients (10) to (14) until uniform, and step C of adding B to A and emulsifying.

| Formulation | % |
| --- | --- |
| (1) Alkyl-modified, partially crosslinked polyether-modified silicone composition *1 | 2 |
| (2) Alkyl-modified, partially crosslinked dimethylpolysiloxane composition *2 | 10 |

-continued

| Formulation | % |
| --- | --- |
| (3) Alkyl branched polyglycerin-modified silicone *3 | 2 |
| (4) Cyclopentasiloxane | 7 |
| (5) Ethylhexyl methoxycinnamate | 7 |
| (6) Hexyl diethylaminohydroxy-benzoylbenzoate | 3 |
| (7) Distearyldimonium hectorite | 0.6 |
| (8) Highly polymerized methylpolysiloxane composition *4 | 3 |
| (9) Hybrid silicone composite powder *5 | 7 |
| (10) Butylene glycol | 6 |
| (11) Sodium citrate | 0.2 |
| (12) Sodium chloride | 1 |
| (13) Phenoxyethanol | 0.3 |
| (14) Purified water | balance |
| Total | 100.0 |

*1 alkyl-modified, partially crosslinked polyether-modified silicone composition: KSG-330 (crosslink 20%, triethylhexanoin 80%) by Shin-Etsu Chemical Co., Ltd.
*2 alkyl-modified, partially crosslinked dimethylpolysiloxane composition: KSG-43 (crosslink 30%, triethylhexanoin 70%) by Shin-Etsu Chemical Co., Ltd.
*3 alkyl branched polyether-modified silicone: KF-6048 by Shin-Etsu Chemical Co., Ltd.
*4 highly polymerized methylpolysiloxane composition: KF-9014 (solid 15%, cyclopentasiloxane 85%) by Shin-Etsu Chemical Co., Ltd.
*5 hybrid silicone composite powder: KSP-105 by Shin-Etsu Chemical Co., Ltd.
total of components (a) and (b) = 10
(a)/(b) = 0.43

It was found that the resulting W/O primer cream was excellent in uneven texture correction, feel-on-use, spread, and adhesion, and left no powder residues.

Example 16

W/O Primer Cream

<Preparation of Cosmetic Composition>

A W/O primer cream was prepared by step A of mixing ingredients (1) to (8) until uniform, step B of mixing ingredients (9) to (13) until uniform, and step C of adding B to A and emulsifying.

| Formulation | % |
| --- | --- |
| (1) Partially crosslinked polyether-modified silicone composition *1 | 3.5 |
| (2) Partially crosslinked dimethylpolysiloxane composition *2 | 10 |
| (3) Silicone branched polyether-modified silicone *3 | 2 |
| (4) Methyl trimethicone *4 | 2 |
| (5) Dimethylpolysiloxane (6 cs) | 7 |
| (6) Acrylic-silicone base graft copolymer composition *5 | 3 |
| (7) Ethylhexyl methoxycinnamate | 5 |
| (8) Alkyl-modified hybrid silicone composite powder *6 | 10 |
| (9) Ethanol | 6 |
| (10) Sodium citrate | 0.2 |
| (11) Sodium chloride | 1 |
| (11) Methyl paraben | 0.15 |
| (13) Purified water | balance |
| Total | 100.0 |

*1 partially crosslinked polyether-modified silicone composition: KSG-210 (crosslink 25%, dimethylpolysiloxane (6 cs) 75%) by Shin-Etsu Chemical Co., Ltd.
*2 partially crosslinked dimethylpolysiloxane composition: KSG-16 (crosslink 25%, dimethylpolysiloxane (6 cs) 75%) by Shin-Etsu Chemical Co., Ltd.
*3 silicone branched polyether-modified silicone: KF-6028 by Shin-Etsu Chemical Co., Ltd.
*4 methyl trimethicone: TMF-1.5 by Shin-Etsu Chemical Co., Ltd.
*5 acrylic-silicone base graft copolymer composition: KP-549 (solid 40%, methyl trimethicone 60%) by Shin-Etsu Chemical Co., Ltd.
*6 alkyl-modified hybrid silicone composite powder: KSP-441 by Shin-Etsu Chemical Co., Ltd.
total of components (a) and (b) = 12.5
(a)/(b) = 0.25

It was found that the resulting W/O primer cream was excellent in uneven texture correction, feel-on-use, spread, and adhesion, and left no powder residues.

Example 17

W/O Primer Cream

<Preparation of Cosmetic Composition>

A W/O primer cream was prepared by step A of mixing ingredients (1) to (5) until uniform, step B of mixing ingredients (8) to (12) until uniform, and step C of adding B to A, emulsifying them, and adding ingredients (6) and (7) thereto.

| Formulation | % |
| --- | --- |
| (1) Partially crosslinked polyglycerin-modified silicone composition *1 | 3.5 |
| (2) Partially crosslinked dimethylpolysiloxane composition *2 | 10 |
| (3) Silicone/alkyl branched polglycerin-modified silicone *3 | 2 |
| (4) Cyclopentasiloxane | 10 |
| (5) Phenyl-modified hybrid silicone composite powder *4 | 10 |
| (6) Metal soap-treated microparticulate titanium oxide composition *5 | 5 |
| (7) Silicone-treated microparticulate zinc oxide composition *6 | 10 |
| (8) Ethanol | 6 |
| (9) Sodium citrate | 0.5 |
| (10) Magnesium sulfate | 0.5 |
| (11) Methyl paraben | 0.15 |
| (12) Purified water | balance |
| Total | 100.0 |

*1 partially crosslinked polyether-modified silicone composition: KSG-710 (crosslink 25%, dimethylpolysiloxane (6 cs) 75%) by Shin-Etsu Chemical Co., Ltd.
*2 partially crosslinked dimethylpolysiloxane composition: KSG-16 (crosslink 25%, dimethylpolysiloxane (6 cs) 75%) by Shin-Etsu Chemical Co., Ltd.
*3 silicone branched polyglycerin-modified silicone: KF-6105 by Shin-Etsu Chemical Co., Ltd.
*4 phenyl-modified hybrid silicone composite powder: KSP-300 by Shin-Etsu Chemical Co., Ltd.
*5 metal soap-treated microparticulate titanium oxide composition: SPD-T5 by Shin-Etsu Chemical Co., Ltd.
*6 silicone-treated microparticulate zinc oxide composition: SPD-Z5 by Shin-Etsu Chemical Co., Ltd.
total of components (a) and (b) = 12.5
(a)/(b) = 0.25

It was found that the resulting W/O primer cream was excellent in uneven texture correction, feel-on-use, spread, and adhesion, and left no powder residues.

Example 18

Mousse Concealer

<Preparation of Cosmetic Composition>

A mousse concealer was prepared by step A of mixing ingredients (6) to (11) on a three-roll mill until uniform, and step B of mixing A with ingredients (1) to (5) until uniform.

| Formulation | % |
| --- | --- |
| (1) Silicone/alkyl-co-modified, partially crosslinked dimethylpolysiloxane composition *1 | 35 |
| (2) Trimethylsiloxysilicic acid composition *2 | 10 |
| (3) Poly(methyl methacrylate) | 2 |
| (4) Hybrid silicone composite powder *3 | 12 |
| (5) Hybrid silicone composite powder *4 | 4 |
| (6) Dimethylpolysiloxane (6 cs) | 15 |
| (7) Metal soap-treated microparticulate titanium oxide | 9 |
| (8) Silicone-treated titanium oxide *5 | 6 |
| (9) Silicone-treated iron oxide *5 | 1 |

-continued

| Formulation | % |
|---|---|
| (10) Silicone-treated mica *5 | 1 |
| (11) Silicone-treated talc *5 | balance |
| Total | 100.0 |

*1 silicone/alkyl-modified, partially crosslinked dimethylpolysiloxane composition: KSG-045Z (crosslink 20%, cyclopentasiloxane 80%) by Shin-Etsu Chemical Co., Ltd.
*2 trimethylsiloxysilicic acid composition: KF-9021 (solid 50%, decamethylcyclopentasiloxane 50%) by Shin-Etsu Chemical Co., Ltd.
*3 hybrid silicone composite powder: KSP-100 by Shin-Etsu Chemical Co., Ltd.
*4 hybrid silicone composite powder: KSP-105 by Shin-Etsu Chemical Co., Ltd.
*5 silicone-treated powder: hydrophobic powder surface-treated with KF-9909 by Shin-Etsu Chemical Co., Ltd.
total of components (a) and (b) = 23
(a)/(b) = 0.44

It was found that the resulting mousse concealer was excellent in uneven texture correction, feel-on-use, spread, and adhesion, and left no powder residues.

Example 19

Stick Concealer

<Preparation of Cosmetic Composition>

A stick concealer was prepared by step A of mixing ingredients (1) to (5) on a disper until uniform, and step B of mixing A with ingredients (6) and (7) at 90° C. until uniform, filling a stick container therewith, and slowly cooling.

| Formulation | % |
|---|---|
| (1) Partially crosslinked dimethylpolysiloxane composition *1 | 22 |
| (2) Silicone spherical powder composition *2 | 10 |
| (3) Hybrid silicone composite powder *3 | 12 |
| (4) Polymethylsilsesquioxane *4 | 18 |
| (5) Dimethylpolysiloxane (6 cs) | 24 |
| (6) Ceresin | 10 |
| (7) Microcrystalline wax | 4 |
| Total | 100.0 |

*1 (modified) partially crosslinked dimethylpolysiloxane composition: KSG-19 (crosslink 15%, dimethylpolysiloxane (6 cs) 85%) by Shin-Etsu Chemical Co., Ltd.
*2 silicone spherical powder composition: KSG-016F (spherical particles 25%, dimethylpolysiloxane (6 cs) 75%) by Shin-Etsu Chemical Co., Ltd.
*3 hybrid silicone composite powder: KSP-411 by Shin-Etsu Chemical Co., Ltd.
*4 polymethylsilsesquioxane: KMP-590 by Shin-Etsu Chemical Co., Ltd.
total of components (a) and (b) = 15.3
(a)/(b) = 0.28

It was found that the resulting stick concealer was excellent in uneven texture correction, feel-on-use, spread, and adhesion, and left no powder residues.

Example 20

Bouncy Foundation

<Preparation of Cosmetic Composition>

A bouncy foundation was prepared by step A of mixing ingredients (5) to (8) on a three-roll mill until uniform, and step B of mixing A with ingredients (1) to (4) and (9) on a kneader until uniform.

| Formulation | % |
|---|---|
| (1) Partially crosslinked dimethylpolysiloxane composition *1 | 20 |
| (2) Hybrid silicone composite powder *2 | 9.5 |
| (3) Polymethylsilsesquioxane *3 | 0.5 |
| (4) Ethylhexyl methoxycinnamate | 2 |
| (5) Acrylic-silicone base graft copolymer composition *4 | 0.1 |
| (6) Triethylhexanoin | 6 |
| (7) Silicone-treated titanium oxide *5 | 20 |
| (8) Silicone-treated iron oxide *5 | 4 |
| (9) Silicone-treated talc *5 | balance |
| Total | 100.0 |

*1 partially crosslinked dimethylpolysiloxane composition: KSG-16 (crosslink 25%, dimethylpolysiloxane (6 cs) 75%) by Shin-Etsu Chemical Co., Ltd.
*2 hybrid silicone composite powder: KSP-100 by Shin-Etsu Chemical Co., Ltd.
*3 polymethylsilsesquioxane: KMP-590 by Shin-Etsu Chemical Co., Ltd.
*4 acrylic-silicone base graft copolymer composition: KP-578 by Shin-Etsu Chemical Co., Ltd.
*5 silicone-treated powder: hydrophobic powder surface-treated with KF-9901 by Shin-Etsu Chemical Co., Ltd.
total of components (a) and (b) = 14.5
(a)/(b) = 0.53

It was found that the resulting bouncy foundation was excellent in uneven texture correction, feel-on-use, spread, and adhesion, and left no powder residues.

Example 21

Gel Eye Color

<Preparation of Cosmetic Composition>

A gel eye color was prepared by step A of mixing ingredients (1) to (3) at 80° C. until uniform, step B of mixing A with ingredients (4) and (5) at 60° C. until uniform, and step C of mixing B with ingredients (6) to (11) until uniform.

| Formulation | % |
|---|---|
| (1) Isotridecyl isononanoate | 24 |
| (2) Squalane | 19.9 |
| (3) Dextrin palmitate *1 | 10 |
| (4) Partially crosslinked dimethylpolysiloxane composition *2 | 12 |
| (5) Hydrophobic anhydrous silica *3 | 0.1 |
| (6) Hybrid silicone composite powder *4 | 8 |
| (7) Polymethylsilsesquioxane *5 | 2 |
| (8) Barium sulfate | 5 |
| (9) Silicone-treated synthetic mica *6 | 13 |
| (10) Glass powder | 7 |
| (11) PET/Al laminate | 4.5 |
| Total | 100.0 |

*1 dextrin palmitate: Leopearl by Chiba Flour Milling Co., Ltd.
*2 partially crosslinked dimethylpolysiloxane composition: KSG-16 (crosslink 25%, dimethylpolysiloxane (6 cs) 75%) by Shin-Etsu Chemical Co., Ltd.
*3 hydrophobic anhydrous silica: Aerosil R972 by Nippon Aerosil Co., Ltd.
*4 hybrid silicone composite powder: KSP-100 by Shin-Etsu Chemical Co., Ltd.
*5 polymethylsilsesquioxane: KMP-590 by Shin-Etsu Chemical Co., Ltd.
*6 silicone-treated powder: hydrophobic powder surface-treated with KP-574 by Shin-Etsu Chemical Co., Ltd.
total of components (a) and (b) = 11
(a)/(b) = 0.38

It was found that the resulting gel eye color was excellent in uneven texture correction, feel-on-use, spread, and adhesion, and left no powder residues.

Example 22

Lip and Cheek

<Preparation of Cosmetic Composition>

A lip and cheek was prepared by step A of mixing ingredients (1) to (5) until uniform, step B of mixing ingredients (8) to (12) on a three-roll mill until uniform, and step C of mixing A and B with ingredients (6) and (7) until uniform.

| Formulation | % |
|---|---|
| (1) Partially crosslinked dimethylpolysiloxane composition *1 | 35 |
| (2) Partially crosslinked dimethylpolysiloxane composition *2 | 10 |
| (3) Dimethylpolysiloxane (6 cs) | balance |
| (4) Silicone branched polyether-modified silicone *3 | 1 |
| (5) Disteardimonium hectorite | 0.6 |
| (6) Hybrid silicone composite powder *4 | 14.5 |
| (7) Polymethylsilsesquioxane *5 | 2 |
| (8) Polyglyceryl-2 triisostearate | 3 |
| (9) Mica | 1.4 |
| (10) Red #202 | 3 |
| (11) Yellow #4 | 1 |
| (12) Red #201 | 0.3 |
| Total | 100.0 |

*1 (modified) partially crosslinked dimethylpolysiloxane composition: KSG-19 (crosslink 15%, dimethylpolysiloxane (6 cs) 85%) by Shin-Etsu Chemical Co., Ltd.
*2 partially crosslinked dimethylpolysiloxane composition: KSG-16 (crosslink 25%, dimethylpolysiloxane (6 cs) 75%) by Shin-Etsu Chemical Co., Ltd.
*3 silicone branched polyether-modified silicone: KF-6028 by Shin-Etsu Chemical Co., Ltd.
*4 hybrid silicone composite powder: KSP-101 by Shin-Etsu Chemical Co., Ltd.
*5 polymethylsilsesquioxane: KMP-590 by Shin-Etsu Chemical Co., Ltd.
total of components (a) and (b) = 22.25
(a)/(b) = 0.53

It was found that the resulting lip and cheek was excellent in uneven texture correction, feel-on-use, spread, and adhesion, left no powder residues, and gave a natural finish.

Example 23

O/W Primer Cream

<Preparation of Cosmetic Composition>

A O/W primer cream was prepared by step A of mixing ingredients (3) to (10) until uniform, step B of mixing ingredients (1) and (2) until uniform, and step C of adding B to A and emulsifying.

| Formulation | % |
|---|---|
| (1) Alkyl-modified, partially crosslinked dimethylpolysiloxane composition *1 | 12 |
| (2) Hybrid silicone composite powder *2 | 7 |
| (3) Polysolvate-60 | 2 |
| (4) Sodium acrylate/sodium acryloyldimethyltaurate copolymer composition *3 | 1 |
| (5) (Ammonium acryloyldimethyltaurine/VP) copolymer 2% solution | 15 |
| (6) Butylene glycol | 10 |
| (7) Glycerin | 3 |
| (8) Pentylene glycol | 1 |
| (9) Methyl paraben | 0.15 |
| (10) Purified water | balance |
| Total | 100.0 |

*1 alkyl-modified, partially crosslinked dimethylpolysiloxane composition: KSG-43 (crosslink 30%, triethylhexanoin 70%) by Shin-Etsu Chemical Co., Ltd.
*2 hybrid silicone composite powder: KSP-105 by Shin-Etsu Chemical Co., Ltd.
*3 Sodium acrylate/sodium acryloyldimethyltaurate copolymer composition: Simulgel EG (crosslink 37.5%) by SEPPIC
total of components (a) and (b) = 10.6
(a)/(b) = 0.51

It was found that the resulting O/W primer cream was excellent in uneven texture correction, feel-on-use, spread, and adhesion, and left no powder residues.

The invention claimed is:

1. An uneven texture-correcting emulsion cosmetic composition comprising
    (a) a partially crosslinked organopolysiloxane,
    (b) an oil-absorbing silicone composite spherical powder,
    (c) 8 to 85% by weight of an oil having a viscosity of 1 to 100 mm$^2$/s at 25° C.,
    (d) 0.1 to 5% by weigh of a non-crosslinked silicone surfactant, and
    (e) water,
    wherein the total amount of components (a) and (b) is 10 to 35% by weight, and a weight ratio (a)/(b) of component (a) to component (b) is from 0.20 to 0.45.

2. The uneven texture-correcting emulsion cosmetic composition of claim 1, wherein component (d) is one or more members selected from linear or branched polyoxyethylene-modified organopolysiloxane, linear or branched polyoxyethylenepolyoxypropylene-modified organopolysiloxane, linear or branched polyoxyethylene/alkyl-co-modified organopolysiloxane, linear or branched polyoxyethylenepolyoxypropylene/alkyl-co-modified organopolysiloxane; and polyglycerin-modified silicones such as linear or branched polyglycerin-modified organopolysiloxane, and linear or branched polyglycerin/alkyl-co-modified organopolysiloxane.

3. The uneven texture-correcting emulsion cosmetic composition of claim 1, wherein component (d) is branched polyoxyethylenepolyoxypropylene/alkyl-co-modified organopolysiloxane.

4. The uneven texture-correcting emulsion cosmetic composition of claim 1, the content of component (d) is 0.2 to 5% by weight of the overall uneven texture correcting cosmetic composition.

5. The uneven texture-correcting emulsion cosmetic composition of claim 1 wherein component (b) is one or more members selected from (vinyl dimethicone/methicone silsesquioxane) crosspolymer, (diphenyl dimethicone/vinyldiphenyl dimethicone/silsesquioxane) crosspolymer, polysilicone-22, and polysilicone-1 crosspolymer, as defined by the nomenclature of cosmetic ingredients.

6. The uneven texture-correcting emulsion cosmetic composition of claim 1, wherein component (b) is one or more members selected from (vinyl dimethicone/methicone silsesquioxane) crosspolymer, and (diphenyl dimethicone/vinyldiphenyl dimethicone/silsesquioxane) crosspolymer, as defined by the nomenclature of cosmetic ingredients.

7. The uneven texture-correcting emulsion cosmetic composition of claim 1, wherein the emulsion is present as a O/W, W/O, or W/O/W type emulsion.

8. The uneven texture-correcting emulsion cosmetic composition of claim 1, further comprising (e) a pigment having a refractive index of at least 1.8 (exclusive of component (b)).

9. The uneven texture-correcting emulsion cosmetic composition of claim 1, further comprising (f) a spherical powder other than components (b) and (e).

10. The uneven texture-correcting emulsion cosmetic composition of claim 1 wherein component (c) is a silicone oil.

* * * * *